United States Patent [19]

Choksi et al.

[11] 4,386,948
[45] Jun. 7, 1983

[54] FILTER DRIVE

[75] Inventors: Pradip V. Choksi, Northridge; Alan A. Davidner, Claremont; Claude A. Vidal, Los Angeles, all of Calif.

[73] Assignee: American Hospital Supply Corporation, Evanston, Ill.

[21] Appl. No.: 304,515

[22] Filed: Sep. 21, 1981

Related U.S. Application Data

[63] Continuation of Ser. No. 105,842, Dec. 20, 1979, abandoned.

[51] Int. Cl.³ .................... B01D 46/52; A61M 16/00
[52] U.S. Cl. ........................................ 55/499; 55/501; 55/502; 55/505; 55/521; 55/528; 55/DIG. 31; 55/DIG. 35; 210/493.3; 210/493.5; 210/445; 210/450; 128/205.12; 128/205.29
[58] Field of Search .................. 55/497–502, 55/505, 521, 527, 528, DIG. 31, DIG. 35; 210/493.1, 493.3, 445, 446, 451, 500.1, 493.5; 128/205.28, 205.29, 205.12

[56] References Cited

U.S. PATENT DOCUMENTS

| | | | |
|---|---|---|---|
| 1,781,254 | 11/1930 | Stelzner | 55/521 |
| 1,888,343 | 11/1932 | Bohlman et al. | 285/399 |
| 2,907,407 | 10/1959 | Engle et al. | 55/500 |
| 3,164,456 | 1/1965 | Brainerd, Jr. et al. | 55/499 |
| 3,556,097 | 1/1971 | Wallace | 128/188 |
| 3,606,739 | 9/1971 | Peterson | 55/484 |
| 3,713,440 | 1/1973 | Nicholes | 128/188 |
| 3,815,754 | 6/1974 | Rosenberg | 210/445 |
| 3,867,294 | 2/1975 | Pall et al. | 210/489 |
| 3,873,288 | 3/1975 | Wachter et al. | 55/497 |
| 3,932,153 | 1/1976 | Byrns | 55/511 |
| 3,960,148 | 1/1976 | Dryden | 128/188 |
| 4,020,230 | 4/1977 | Mahoney et al. | 55/527 |
| 4,133,656 | 1/1979 | Kippel | 55/274 |
| 4,159,954 | 7/1979 | Gangemi | 210/146 |
| 4,184,966 | 1/1980 | Pall | 210/493.3 |
| 4,187,182 | 2/1980 | Rosenberg | 210/445 |
| 4,197,099 | 4/1980 | Lundberg | 55/378 |

FOREIGN PATENT DOCUMENTS

| | | | |
|---|---|---|---|
| 693390 | 6/1940 | Fed. Rep. of Germany | 55/497 |
| 2162355 | 6/1973 | Fed. Rep. of Germany | 55/502 |
| 53-114976 | 10/1978 | Japan | 55/521 |
| 750099 | 6/1956 | United Kingdom | 210/493.2 |
| 780709 | 8/1957 | United Kingdom . | |
| 780710 | 8/1957 | United Kingdom . | |
| 873130 | 7/1961 | United Kingdom | 55/500 |
| 892262 | 3/1962 | United Kingdom . | |
| 602157 | 7/1978 | United Kingdom | 55/497 |
| 1542425 | 3/1979 | United Kingdom | 55/502 |

Primary Examiner—David L. Lacey
Attorney, Agent, or Firm—Roger A. Williams

[57] ABSTRACT

A filter device used to filter medical anesthesia gases and other inhalable respiratory gases. The filter device has a ported housing, and a filter member within the housing. The filter member is a porous sheet that is transversely pleated and draped to define a peripheral foot of such porous sheet. The peripheral foot is sealed along its entire periphery to the housing. Two sets of intermeshing hangers are provided with both sets of the hangers being anchored to the housing and distortingly maintaining the porous sheet in such a pleated condition.

25 Claims, 9 Drawing Figures bural adapters. However, in the past, such small filters have had a very high pressure drop of 3 inches of water at 12.5 L gas per minute flow rate. Such high pressure drop limited the use of such a filter to inhalation therapy use where a pump or other mechanism forced air into the patient's lungs and then extracted it by vacuum. It was not suited for anesthesia use in which the anesthesia gases are transferred across the filter by normal breathing of the patient.
FILTER DRIVE This application is a continuation of application Ser. No. 105,842, filed Dec. 20, 1979, now abandoned.

BACKGROUND

Filters have been proposed for use in anesthesia equipment to filter out bacteria and other microorganisms from inhaled anesthesia gases. One example is U.S. Pat. No. 3,556,097, which shows in FIGS. 11–15 a large filter that is currently on the market. One of the problems with such filter is that it has a very large dead space of 150 to 200 cubic centimeters in the filter excluding the tubular fitments on each end of the filter. With such large dead space, the patient is rebreathing a substantial portion of his exhaled respiratory gases.

It is desirable to have an anesthesia filter with less than 50 cubic centimeters of dead space, excluding tubular adapters. However, in the past, such small filters have had a very high pressure drop of 3 inches of water at 12.5 L gas per minute flow rate. Such high pressure drop limited the use of such a filter to inhalation therapy use where a pump or other mechanism forced air into the patient's lungs and then extracted it by vacuum. It was not suited for anesthesia use in which the anesthesia gases are transferred across the filter by normal breathing of the patient.

Even with such high pressure drop filters, as shown in U.S. Pat. No. 3,815,754, there was a difficult manufacturing procedure to completely seal the filter within the rectangular housing. Separate end plates (30 and 31 of FIG. 1) were required to seal the serpentine edges of the pleated filter.

SUMMARY OF THE INVENTION

The present invention overcomes the problems of prior anesthesia filters mentioned above. This invention includes a rectangular, box-like housing in which a transversely pleated filter sheet of very low pressure drop, such as a nonwoven polypropylene sheet, is pleated to provide a draped peripheral foot portion that is sandwiched between two sections of the filter housing and sealed to such housing. The housing has two sets of internal hangers that maintain the filter member in pleated condition with spaces between the pleats for high volume gas flow at a low pressure drop. The housing is very compact and has 50 cubic centimeters or less internal volume dead space excluding the tubular adapters.

RELATED APPLICATIONS

Anesthesia System and Method of Filtering Respiratory Gas, filed Dec. 20, 1979, Ser. No. 105,841, by Choksi, Notice of Allowance mailed June 8, 1982; Method of Making a Filter, filed Dec. 20, 1979, Ser. No. 105,840, by Choksi et al; and Bacterial Filter Media, filed Dec. 20, 1979, Ser. No. 105,819, by Choksi et al, all of which are commonly assigned to the same assignee as this application.

THE DRAWINGS

FIG. 1 is a side elevational view of the filter housing shown partially in section;
FIG. 2 is a reduced top elevational view of FIG. 1;
FIG. 3 is a reduced bottom elevational view of FIG. 1;
FIG. 4 is a sectional view of a side wall portion of the housing showing a first set of hangers;
FIG. 5 is a sectional view of the side wall portion of the housing taken at 90° to the view in FIG. 4;
FIG. 6 is a side elevational view of the filter member in pleated condition;
FIG. 7 is a view of the filter member taken at 90° to the view of FIG. 6;
FIG. 8 is a side elevational view of a base of the housing showing a second set of hangers; and
FIG. 9 is a view of the base taken at 90° to the view of FIG. 8.

DETAILED DESCRIPTION

Figure 1:
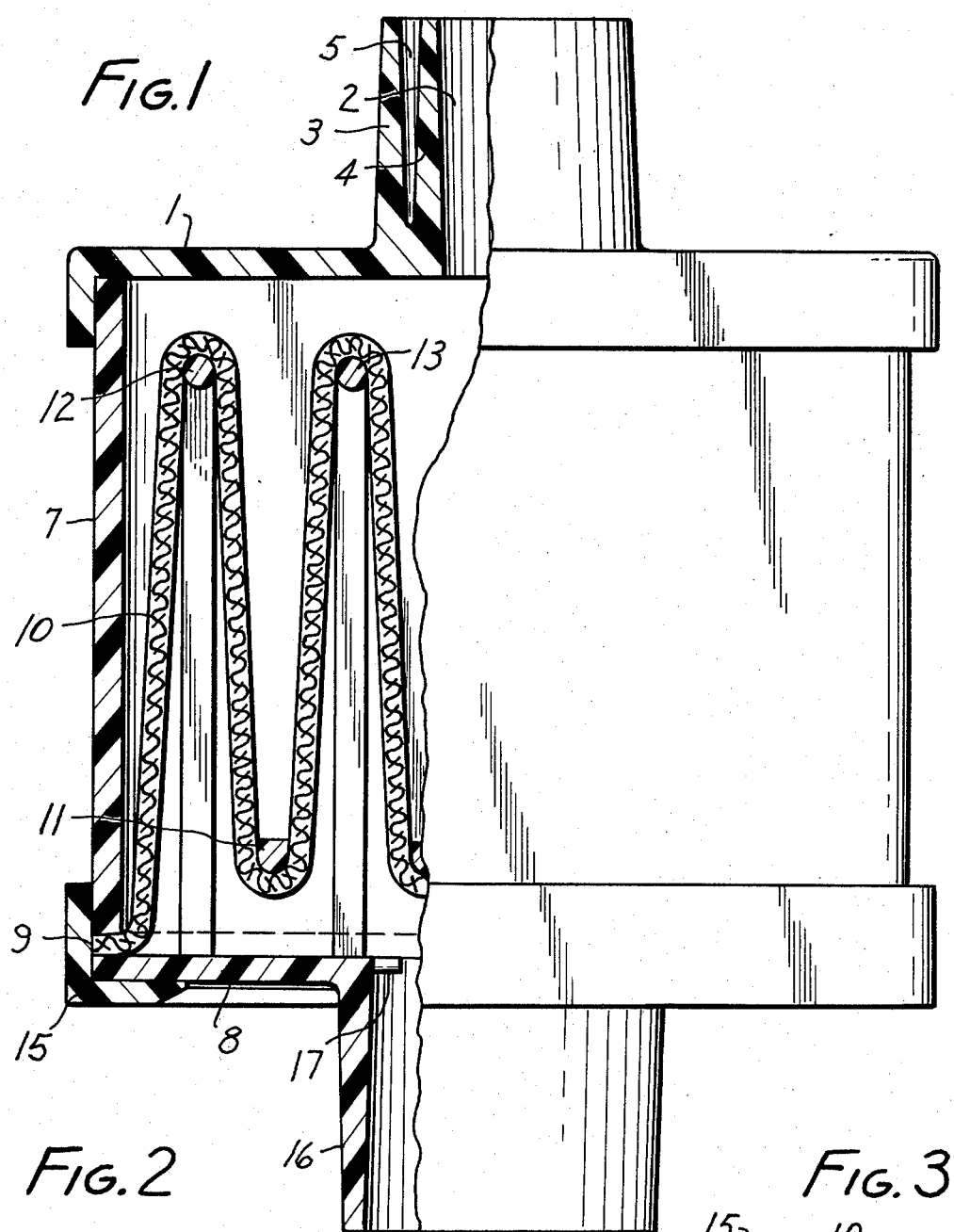

In FIG. 1, a filter housing is shown which includes a top 1 with a port 2. Defining this port is a pair of upstanding tubular elements 3 and 4 having an annular space 5 therebetween. Space 5 prevents undue distortion of the tubular coupling member surrounding port 2. Preferably, both an internal surface of tubular member 4 and outer surface of tubular member 3 are slightly tapered for coupling with various medical equipment, such as anesthesia hoses, masks, endotracheal tubes, etc..

The top 1 is sealed to rectangular side wall 7. Side wall 7 is in turn sealed at its lower end to a base 8 through a sandwiched seal with a rectangular foot portion 9 of pleated filter member 10. A microorganism filter member 10 is held in pleated condition by a first set of hangers, one of which is shown at 11, and a second set of hangers, two of which are shown at 12 and 13. The first set of hangers are attached to rectangular side wall 7 and the second set of hangers are attached to base 8. The hanger configuration is more clearly shown in FIGS. 4, 5, 8, and 9.

Covering an exposed end of the peripheral foot 9 of filter member 10 is a collar member 15 secured to base 8. Also connected to base 8 is a tubular adapter 16 which preferably has a series of internal lugs 17 to prevent overinsertion of a coupling member into adapter 16. Preferably, adapter 16 has an internal tapered surface for wedgingly connecting to other adapters and conduits.

Figure 2:
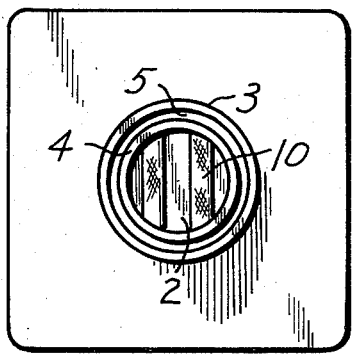
Figure 3:
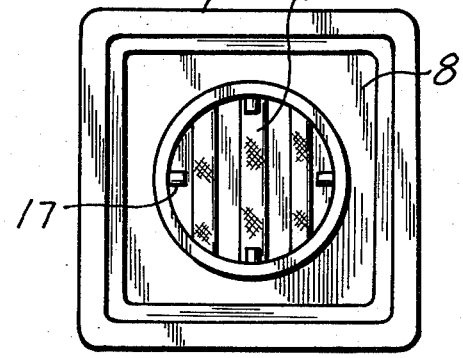

FIGS. 2 and 3 show the top view of the rectangular shaped housing in which upper edges of the pleats of filter member 10 are shown through port 2. FIG. 3 shows the bottom view of the rectangular housing with lugs, such as 17, protecting the pleated filter member 10.

Figure 4:
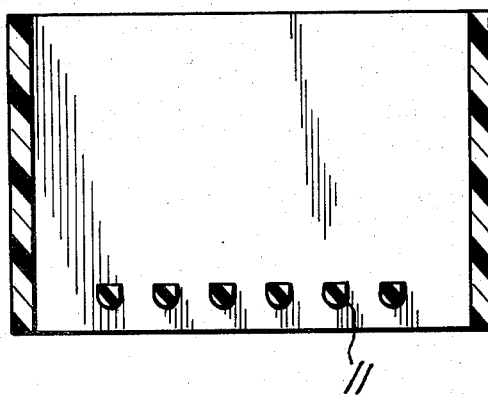
Figure 5:
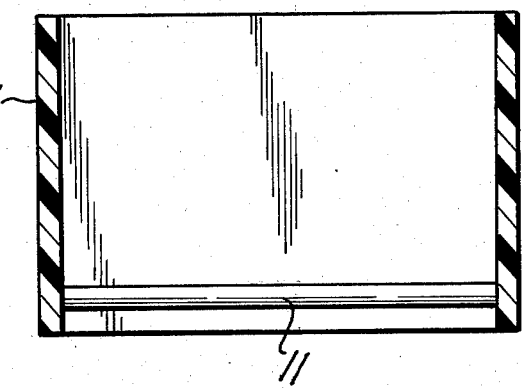

In FIGS. 4 and 5, the construction of the side wall is shown to be as a generally rectangular member with a series of bars, such as 11, extending across a major portion of the housing, such as between opposite sides of the rectangular side wall. Preferably, these bars have rounded bottom edges holding the pleats of the filter member without undue creasing or wrinkling.

Figure 6:
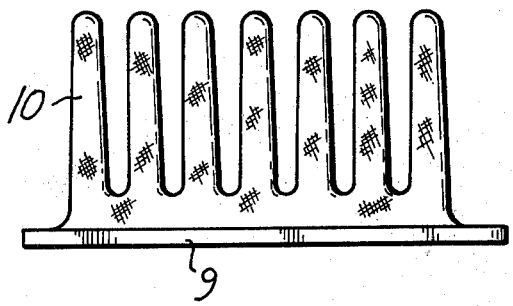
Figure 7:
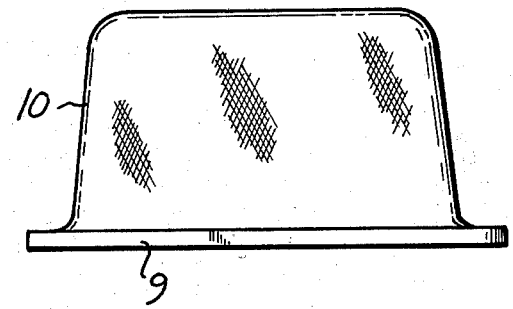

FIGS. 6 and 7 show the general configuration of the pleated filter member which begins as a flat sheet and is distorted into its pleated condition by the interaction of the two sets of hangers. It is important to note that the peripheral foot 9 of the pleated filter member extends about the complete periphery of the filter member. This is necessary to get a complete seal about the filter member so that there is no gas leakage around the filter member 10.

Figure 8:
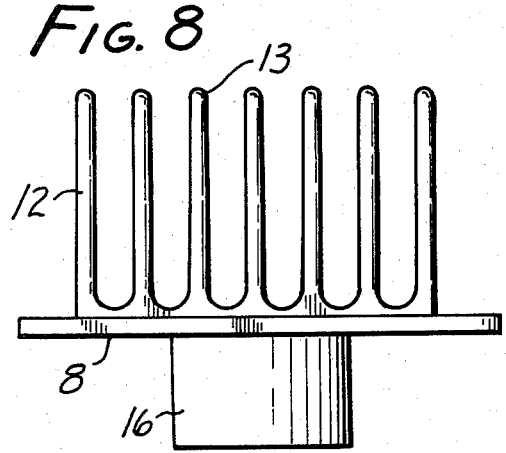
Figure 9:
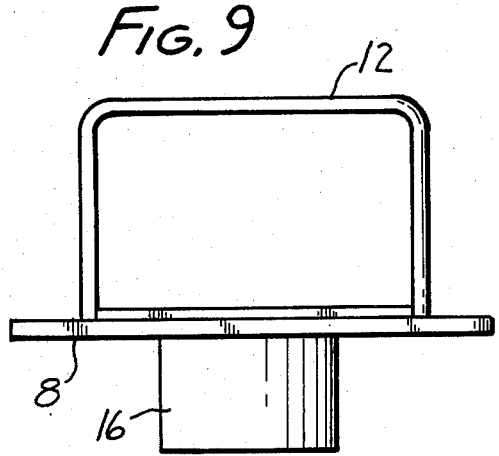

In FIGS. 8 and 9, the base 8 is shown which has the second series of hangers, such as 12 and 13, which are generally U-shaped as shown in FIG. 9. When the filter housing is assembled as shown in FIG. 1, the first and second sets of hangers cooperate to form the pleated or serpentine configuration of the filter member which is firmly sealed about its entire peripheral foot area.

The filter housing and filter member work very well when the housing is constructed of injection molded polypropylene thermoplastic material and the filter media 10 is of a melt blown nonwoven polypropylene material. This material is naturally hydrophobic without additional treatment. The specific details of the filter media is described in the above co-pending, co-owned application by Choksi and Davidner. Because both the filter media and the filter housing are of polypropylene material, a very firm and reliable seal can be made between these two materials. Ultrasonic sealing has been used very effectively in the seal, but other forms of heat or fusion sealing could be used.

With the above construction, a very effective filter for use in anesthesia gas circuits or other medical respiratory gas filtering uses has been provided. The filter housing has an internal volume of 50 cubic centimeters or less and has a pressure drop of less than 0.3 inch of water at gas flow rates up to 12.5 L gas/minute. These slower rates and pressure drops can occur with many different concentrations of inhalant gases, including inhalant anesthetics. Tests have been run with pressure drops of approximately 0.2 inch of water.

In the foregoing description, a specific example has been used to describe the invention. It is understood by those skilled in the art that certain modifications can be made to this example without departing from the spirit and scope of the invention.

We claim:

1. A filter device comprising: a housing having an inlet port and an outlet port; a filter member within the housing, which filter member comprises a porous sheet transversely pleated and draped to define a peripheral foot of such porous sheet, which peripheral foot is sealed along its entire periphery to the housing; and two sets of intermeshing hangers, both sets of hangers being anchored to the housing and distortingly maintaining the porous sheet in said pleated condition.

2. A filter device as set forth in claim 1, wherein the housing has a peripheral side wall and a base including one of said ports, and the draped peripheral foot portion of the filter member is sandwiched between and sealed to the side wall and base.

3. A filter device as set forth in claim 2, wherein the filter member comprises a porous thermoplastic material and the housing comprises a thermoplastic material that is sealed by a heat fusion seal to the filter member.

4. A filter device as set forth in claim 3, wherein the filter member is a naturally hydrophobic thermoplastic material.

5. A filter device as set forth in claim 4, wherein the filter member is of a nonwoven polypropylene material.

6. A filter device as set forth in claim 1, wherein both the filter member and the housing are of polypropylene material.

7. A filter device as set forth in claim 1, wherein both sets of the hangers engage inner surfaces of folds in the pleats.

8. A filter device as set forth in claim 7, wherein the sets of hangers are spaced apart.

9. A filter device as set forth in claim 8, wherein the spaced hangers are bars extending across a major portion of the housing.

10. A filter device as set forth in claim 9, wherein the housing includes a peripheral side wall and a base, and the hangers include a first set of hangers anchored to the side wall, and a second set of hangers anchored to the base, said two sets of hangers intermeshing to maintain the filter member in said pleated condition.

11. A filter device as set forth in claim 10, wherein the second set of hangers are each generally U-shaped with legs, and the legs of these hangers are anchored to the base.

12. A filter device as set forth in claim 10, wherein the two sets of hangers intermesh with each other in a manner that maintains a space between the pleats.

13. A filter device as set forth in claim 1, wherein the housing comprises a generally rectangular box with a tubular adapter defining said inlet port and a tubular adapter defining said outlet port.

14. A filter device as set forth in claim 13, wherein at least one of the adapters has an internal lug to limit penetration of a coupling member into such adapter.

15. A filter device as set forth in claim 13, wherein the filter housing has an internal volume of 50 cc or less.

16. A filter device as set forth in claim 1, wherein the filter medium is constructed and arranged in said housing so as to provide a pressure drop of less then 0.3 inch water at gas flow rates up to 12.5 gas/minute.

17. A respiratory gas filter comprising: a rectangular housing having an internal volume exclusive of connecting adapters which is 50 cc or less and which housing includes an inlet and an outlet; a microorganism filter member within the housing, which filter member comprises a porous sheet transversely pleated and draped to define a peripheral foot of such porous drape that is sealed along its entire periphery to the housing, said peripheral foot forming a seal extending about the entire periphery of the filter member, which gas filter device has a pressure drop of less than 0.3 inch water at gas flow rates up to 12.5 L gas/minute whereby a respiratory gas can be driven through the filter by normal breathing of a patient with a minimum amount of unfiltered exhaled air being rebreathed by such patient; and two sets of intermeshing hangers, both sets of hangers being anchored to the housing to distortingly maintain the sheet in said pleated condition while the peripheral foot is sealed to the housing.

18. A respiratory gas filter as set forth in claim 17, wherein the pleated filter member comprises a hydrophobic thermoplastic material.

19. A respiratory gas filter as set forth in claim 18, wherein the filter member is a nonwoven polypropylene sheet material.

20. A filter device comprising: a housing having a peripheral side wall; a top end including a port thereon and connected to the side wall; a base end including a port thereon and connected to the side wall; a filter member within the housing, which filter member comprises a porous sheet transversely pleated and draped to define a peripheral foot of such porous sheet that is sealed along its entire periphery between the side wall and one end of the housing; and two sets of intermeshing hangers, both sets being anchored to the housing to distortingly maintain the sheets in said pleated condition while the peripheral foot is sealed to the housing.

21. A filter device as set forth in claim 20, wherein there is a skirt member connected to the housing that covers an exposed edge of the filter member.

22. A filter device with a filter member of a porous sheet sealed to a housing of the device, which housing includes an inlet port and an outlet port, wherein the improvement comprises: said housing comprising at least two joinable portions, first and second sets of hangers in the housing, each set of hangers being anchored to said at least two joinable portions of the housing so that the two sets of hangers can intermesh with each other when said at least two portions are joined to distortingly maintain the filter member in a pleated condition by engaging inner surfaces of folds in the pleats along central and end portions of the pleats so as to maintain spaces between the porous sheet's pleats; and said pleated filter member forming a draped skirt having a peripheral foot extending about the entire periphery of the filter member with the entire peripheral foot permanently sealed between the two joinable portions of the housing.

23. A filter device as set forth in claim 22, wherein the housing has a side wall connected to the first set of hangers and a base end connected to the second set of hangers.

24. A filter device as set forth in claim 23, wherein each hanger of the second set of hangers is generally U-shaped.

25. A filter device comprising: a housing having an inlet port and an outlet port and a top, bottom, and side walls; a filter member within the housing, which filter member comprises a porous sheet transversely pleated and draped within the housing spaced from the top bottom, and side walls, said filter member including a peripheral foot, and the filter member is sealed to the housing along the entire periphery of the peripheral foot; and two sets of intermeshing hangers, both sets of hangers being anchored to the housing and distortingly maintaining the porous sheet in said pleated condition.

* * * * *